(12) United States Patent
Thijssen et al.

(10) Patent No.: US 8,771,649 B2
(45) Date of Patent: Jul. 8, 2014

(54) INDUCIBLE RELEASE VEHICLES

(75) Inventors: Henricus Matheus Wilhelmus Maria Thijssen, Houten (NL); Roy Christiaan Montijn, Amsterdam (NL); Johannes Wilhelmus Timmermans, Ede (NL); Theodoor Maximiliaan Slaghek, Rotterdam (NL); Jacobus Johannes Frederick van Veen, Badhoevedorp (NL); Johannes Wilhelmus Leonardus Boumans, Ouderkerk aan de Amstel (NL)

(73) Assignee: Nederlandse Organisatie voor Toegepast-Natuurwetenschappelijk Onderzoek TNO, Delft (NL)

( * ) Notice: Subject to any disclaimer, the term of this patent is extended or adjusted under 35 U.S.C. 154(b) by 1717 days.

(21) Appl. No.: 10/558,816

(22) PCT Filed: May 28, 2004

(86) PCT No.: PCT/NL2004/000387
§ 371 (c)(1),
(2), (4) Date: Jul. 13, 2006

(87) PCT Pub. No.: WO2004/105485
PCT Pub. Date: Dec. 9, 2004

(65) Prior Publication Data
US 2007/0092480 A1    Apr. 26, 2007

(30) Foreign Application Priority Data

May 30, 2003 (NL) .................. PCT/NL03/00409

(51) Int. Cl.
| | | |
|---|---|---|
| *A01P 3/00* | (2006.01) |
| *A61K 38/00* | (2006.01) |
| *A61P 17/10* | (2006.01) |
| *A61K 9/16* | (2006.01) |
| *A01N 63/00* | (2006.01) |
| *A61K 9/68* | (2006.01) |
| *A61K 47/36* | (2006.01) |
| *A61Q 15/00* | (2006.01) |
| *A61Q 19/00* | (2006.01) |
| *A01N 25/00* | (2006.01) |
| *A23L 1/22* | (2006.01) |
| *A01N 25/04* | (2006.01) |
| *A61K 47/38* | (2006.01) |
| *A01P 1/00* | (2006.01) |
| *A01N 25/10* | (2006.01) |
| *A61K 47/42* | (2006.01) |
| *A61L 9/01* | (2006.01) |

(52) U.S. Cl.
USPC ........... 424/48; 424/76.1; 424/94.1; 514/781; 514/777; 514/1.1; 514/773; 514/778

(58) Field of Classification Search
CPC .. A01N 25/10; A61L 15/46; A61L 2300/208; A61L 2300/404; A61L 2300/604
USPC .............. 424/445, 48, 489, 76.1, 78.09, 94.1; 514/1.1, 773, 774, 777, 778, 781
See application file for complete search history.

(56) References Cited

U.S. PATENT DOCUMENTS

| | | | | |
|---|---|---|---|---|
| 4,783,448 A * | 11/1988 | Johansson | ...................... | 514/57 |
| 4,957,744 A * | 9/1990 | della Valle et al. | ............. | 424/401 |
| 5,077,314 A * | 12/1991 | Philips et al. | ............... | 514/640 |
| 5,226,902 A * | 7/1993 | Bae et al. | .................. | 604/892.1 |
| 5,227,157 A * | 7/1993 | McGinity et al. | .......... | 424/78.02 |
| 5,759,582 A * | 6/1998 | Leong et al. | .................. | 424/492 |
| 5,840,338 A * | 11/1998 | Roos et al. | .................... | 424/488 |
| 5,939,485 A * | 8/1999 | Bromberg et al. | ............. | 524/556 |
| 5,998,176 A * | 12/1999 | Budolfsen et al. | ............. | 435/101 |
| 6,140,475 A * | 10/2000 | Margolin et al. | ............. | 530/402 |
| 6,214,331 B1 * | 4/2001 | Vanderhoff et al. | ........ | 424/78.17 |
| 6,358,525 B1 * | 3/2002 | Guo et al. | ..................... | 424/464 |
| 6,541,606 B2 * | 4/2003 | Margolin et al. | ............. | 530/350 |
| 6,585,993 B2 * | 7/2003 | Donovan et al. | ............. | 424/423 |

FOREIGN PATENT DOCUMENTS

WO    WO 95/33773    12/1995

OTHER PUBLICATIONS

Cowman and Baron. "Influence of Hydrophobicity on Oligopeptide Utilization by Oral Streptocci" J. Dent. Res. 69(12): 1847-1851, Dec. 1990.*

* cited by examiner

*Primary Examiner* — Johann Richter
*Assistant Examiner* — Audrea Buckley
(74) *Attorney, Agent, or Firm* — Preti Flaherty Beliveau & Pachios LLP

(57) ABSTRACT

This invention relates to inducible release vehicle comprised of crosslinked carbohydrates or proteins and an active ingredient. The release is induced by an external stimulus, e.g. an enzyme such as amylase. Such a vehicle can particularly be used in applications for preventing microbial decay or combating microbial infections. Other uses are for oral applications such as providing antdaries or flavoring compounds and for pharmaceutical and/or nutraceutical applications.

30 Claims, 4 Drawing Sheets

INDUCIBLE RELEASE VEHICLES

This application is a §371 national phase filing of PCT/NL2004/000387 filed May 28, 2004, and claims priority to an International Application No. PCT/NL03/00409 filed May 30, 2003.

FIELD OF THE INVENTION

The invention relates to inducible (or on-demand) release vehicles produced from cross-linked polymers. This type of vehicles is particularly usable for packaging an active component in applications in which said active component needs to be shielded from the environment until it is at a time and/or place where it should be released. One of the major applications lies in the field of antimicrobial active components, which need only to be released in the presence of microbial contamination. This can, for instance, be the case in antimicrobial packages, which have as their general object to prolong the storage life of the packaged foods by preventing decay by microorganisms.

BACKGROUND ART

The disadvantage of current prior art antimicrobial packages is that the components are continuously released or are in continuous contact with the foods, also when no microorganisms are present, or are released under the influence of mechanical activity. Presence of (harmful) microorganisms, however, hardly ever involves mechanical activity, so that such a package is not usable for preventing decay of foods.

Similarly, the encapsulation of antimicrobials is known from applications in coatings, paint, cosmetics and general anti-fouling compositions, but here again the currently used vehicles mainly provide for a continuous release of the antimicrobial compound, which is not desirable for environmental reasons: such a continuous release causes an abundance of antimicrobial components in the environment which can give rise to an unwanted increased antibiotic resistance in microbial populations.

Induced release is also preferable in pharmaceutical and/or nutraceutical compositions. It enables high concentrations of active components locally, which means that the total dose to be administered can be decreased. Further, it prevents unwanted or even toxic effects to occur at sites where no medication is needed.

Several vehicles for active ingredients have already been described in the literature, especially in the field of antimicrobial active components. WO 95/17816 describes an edible pest repellent which can be encapsulated in cellulose or derivatives. The active compound is slowly released from said vehicle. GB 2198062 describes a plastic film containing microcapsules with active components, such as insect repellents. However, these capsules need mechanical pressure to release the active ingredient.

Degradable capsules have been disclosed in WO 99/08553, wherein the capsules are made of "edible polymers" such as polyvinylpyrrolidone, polyethylene wax, etc. A special form of degradable capsules is presented in WO 95/33773 in which capsules of chitine or chitosan are presented containing an active ingredient. These capsules would be degradable by lysozyme through hydrolysis. GB 1576999 describes the use of biopolymers, which are coagulated at elevated temperature (120° C.) in "vasiline petroleum gelly" and contain either organic tin compounds or $Cu_2O$. These particles are used as additive in anti fouling paint. The disadvantage of the described system is that for instance heat sensitive and/or organic solvent sensitive active ingredients cannot be used and also the formed capsules cannot be filled with an active ingredient once the vehicle is formed.

Thus, there is still need for alternative vehicles encapsulating an active ingredient which would be able to release their content on demand, i.e. at a specified place and/or time, due to an external (physical, chemical or enzymatical) trigger or stimulus.

SUMMARY OF THE INVENTION

The present invention now provides such alternative vehicles.

The invention relates to an inducible release vehicle comprising a charged cross-linked polymer and an active component wherein the release is triggered by contact of the vehicle with an external stimulus and wherein said polymer is a carbohydrate or a protein. Preferably the active ingredient is incorporated after the vehicle has been isolated.

Preferred embodiments are vehicles wherein the carbohydrate polymer is modified by oxidation, substitution with cationic functional groups or with carboxymethyl groups, or esterification by e.g. acetyl groups, wherein the polymer is chosen form the group consisting of starch or a derivative of starch, cellulose or a derivative of cellulose, pectin or a derivative of pectin, and gelatine or a derivative of gelatine, wherein the cross linker is chosen from the group consisting of divinyl sulphone, epichlorohydrin, a di-epoxide such as glycerol diglycidyl ether or butanedioldiglycidyl ether, sodium trimetaphosphate and adipic acid or derivatives thereof, or wherein the polymer is cross-linked by means of a cross-linking enzyme chosen from the group consisting of peroxidases, laccases, polyphenol oxidases, transglutaminases, protein disulfide isomerases, sulfhydryl oxidases, lysyl oxidases and lipoxygenases and wherein the vehicle is loaded with a charged compound, preferably a charged compound having a molecular weight below 50 kD, or a hydrophobic compound, which in both cases can preferably be an antimicrobial compound or a protein.

A preferred embodiment are vehicles wherein the external stimulus is an enzyme which is able to degrade the polymer, or wherein the release of the active ingredient is induced by change of electrostatic interaction, cause by e.g. a change in the pH or a change in the salt concentration.

The above mentioned vehicles are preferably used in a pharmaceutical and/or nutraceutical composition, more preferred for this use are vehicles which comprise an anti-microbial compound or a cytostatic compound. However, in cases wherein the active component is an anti acne agent or a deodorant, the vehicles can be used as a cosmetic composition.

In another preferred embodiment the vehicles of the invention can be used as a fungicidal paint wherein the active component is a fungicide or an antifouling paint composition wherein the active component is an antifouling component.

An also preferred embodiment is a dressing means, preferably wherein the dressing means is a wound dressing means or a sanitary dressing means and wherein the active component is an antimicrobial compound.

An equally preferred embodiment is a coating comprising the vehicles of the invention, wherein said vehicles comprise an antimicrobial agent.

Another preferred embodiment is use of said vehicles for masking off flavour tasting compounds such as bitter tasting medicine or nutraceuticals. Similarly the vehicles according to the invention can be used for encompassing flavours e.g. for chewing gum. Also a preferred embodiment is use of the vehicle according to the invention for passage through the stomach of an acid- or protease-labile medicine or nutraceutical in the active form.

A vehicle according to the invention can also preferably be used for the immobilization and/or isolation of active or specific components in a solution, specifically for the immobilization of large charged particles, e.g. bacteria, in a solution.

The invention also comprises a method for producing a vehicle according to the invention comprising:
a) providing a polymer and a cross-linker or cross-linking enzyme;
b) activating the cross-linking by addition of base or acid;
c) allowing for cross-linking to occur and gelation of the cross-linked polymer;
d) breaking the gel resulting from step d) into smaller particles;
e) drying the particles from step d) and optionally grinding these into finer particles;
f) loading said particles with an active component.

DETAILED DESCRIPTION OF THE INVENTION

Figure 1:
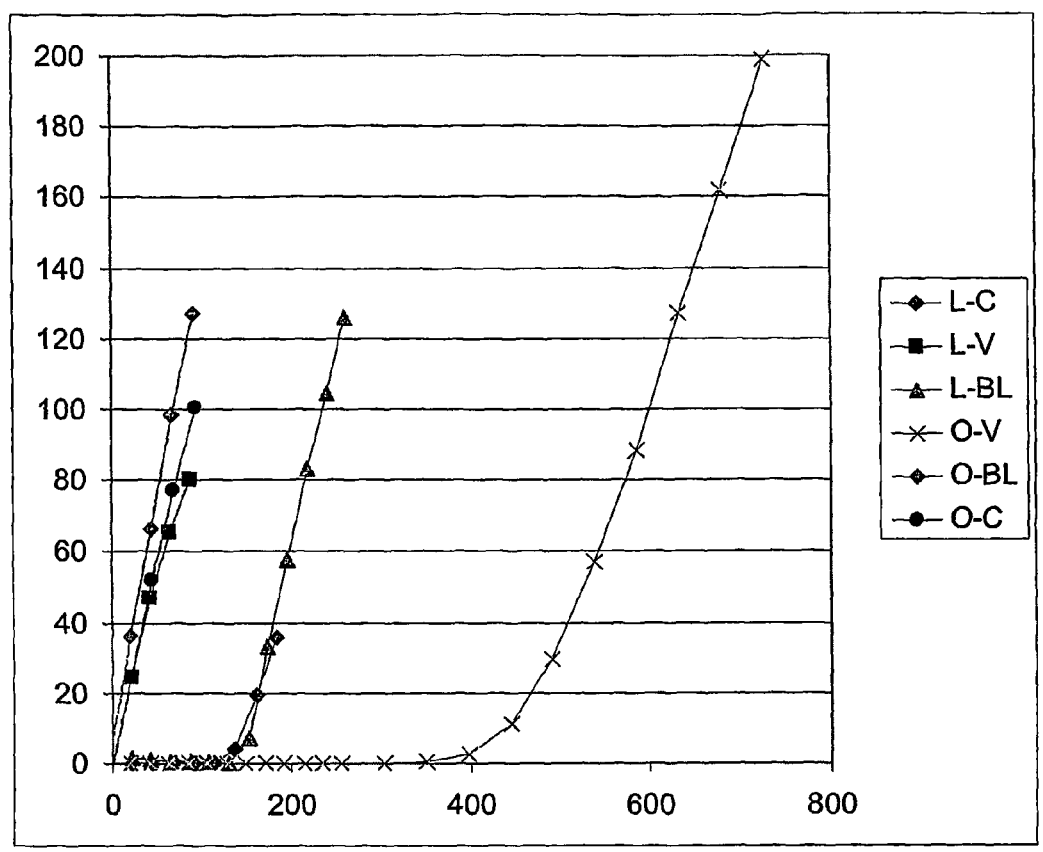
FIG. 1: The amount of lysozyme (L) or ovalbumin (O) in solution as a function of the amount added (mg) to the gels C, V and BL

Vehicles of the invention (also indicated as particles or capsules) comprise a cross-linked carbohydrate or protein, made of oligomeric and polymeric carbohydrates or proteins which can be used as a substrate for any external stimulus, such as an enzyme. Carbohydrates which can thus be used are carbohydrates consisting only of C, H and atoms such as, for instance, glucose, fructose, sucrose, maltose, arabinose, mannose, galactose, lactose and oligomers and polymers of these sugars, cellulose, dextrins such as maltodextrin, agarose, amylose, amylopectin and gums, e.g. guar. Proteins which can be used include albumin, ovalbumin, casein, myosin, actin, globulin, hemin, hemoglobin, myoglobin and small peptides. Preferably, oligomeric carbohydrates from DP2 on or polymeric carbohydrates from DP5O on are used. These can be naturally occurring polymers such as starch (amylose, amylopectin), cellulose and gums or derivates hereof which can be formed by phosphorylation or oxidation. Other polymers can also be used (e.g. caprolactone), which can be added for a better compatibility with e.g. the packaging material. In the case of proteins, proteins obtained from hydrolysates of vegetable or animal material can also be used. Also suitable mixtures of carbohydrates (e.g. copolymers) or mixtures of proteins can be used.

The advantages of cross linked polymers lies in the intrinsic stability of the vehicles formed through the introduction of cross links in the matrix. Specifically, the crosslinks are ether- and/or ester-links, where for the ester-links phosphate-esters are preferable. A further important advantage is that cross-linking provides a three-dimensional lattice of the cross-linked polymer, in which the active component can be "filled in". Moreover, the choice of components, i.e. the choice of polymer(s) and cross-linker(s) influence the three-dimensional structure of the vehicle and thus would allow for the manufacture of specific vehicles suited for molecules of a certain size and/or certain charge.

The polymer matrix from which the vehicle is built may be constructed from readily available and water soluble polymers such as polysaccharides and (hydrolysed) proteins and in doing so a flexible matrix may be formed and positive and/or negative charge through e.g. carboxylic acids and/or cationic groups will generate a custom made vehicle. This cannot be accomplished using polysaccharides such as chitin and/or chitosan. Also the above mentioned polymers are much cheaper than the hitherto used chitin and chitosan. The possession of a charge is a most important feature of a polymer for the present invention. It will greatly facilitate the formation of a complex between the active component (which is often a charged molecule) and the polymer lattice. The charge can be provided by the polymer itself, but—if the polymer does not have a positive or negative charge—the charge can be introduced as a result of modification of the polymer or by the cross-linker used for cross-linking the polymer.

The formation of the matrix is accomplished through covalent cross linking of the polymers. Typical cross linkers, that can be used, are divinyl sulphone, epichlorohydrin, a di-epoxide such as glycerol diglycidyl ether or butanedioldiglycidyl ether, sodium trimetaphosphate and adipic acid or derivatives thereof, and the like. Cross-linking can also be established by enzymatic action, e.g. by using enzymes from the group consisting of laccases (which e.g. induce cross-linking of pectins), peroxidases, polyphenol oxidases, transglutaminases, protein disulfide isomerases, sulfhydryl oxidases, lysyl oxidases and lipoxygenases. Methods how to use these cross-linkers or cross-linking enzymes are well known in the art and/or have been abundantly described in the experimental part.

Modification of the polymers can be accomplished by oxidation, substitution with cationic functional groups or carboxymethyl groups and/or esterifying with e.g. acetyl groups. Although in the latter case no charge is added, it is used to make the polymer more hydrophobic to allow complexing of the polymer with active components that have little or no charge. Generally the polymers will be modified before cross-linking and gelation. Only if cross-linking by ether-forming has been done it is possible to modify the polymer after cross-linking and gelation. The person skilled in the art will know how to modify the polymers specified in the invention to provide them with the mentioned groups.

The charge of the cross-linked polymer can be negative or positive depending on the type of polymer, the type of modification and the type of cross-linking.

Advantageously, the polymers are of considerable size, i.e. 30 kD or more. This allows for the ready formation of a gel upon cross-linking and it allows for the formation of a lattice which is capable of taking up the active component.

The vehicles of the inventions are made by cross-linking readily available carbohydrate polymers and/or proteins. Preferably, the cross-linked polymers form a gel, as shown in the Examples, which ensures a long stability of the vehicles and an easy further employment of the vehicles in the compositions according to the invention, such as medicaments, coatings and dressings.

In general the method of making the particles is as follows:
a) provide a polymer;
b) provide a cross-linker or cross-linking enzyme and activating the cross-linker by addition of a base or an acid;
c) add the cross-linker to the polymer; it is to be understood that activation of the cross-linker may occur before mixing the polymer and the cross-linker, or when both already are mixed. This depends on the type of cross-linker and the type of polymer that is used;
d) allow for cross-linking to occur;
e) allow for gelation of the cross-linked polymer;
f) wash the gel to remove all solvents and reagents that have not reacted;
g) form vehicles from the gel by breaking the gel into smaller particles;
h) dry the vehicles and—if desired—mill them into finer particles
i) load the vehicles with the active component.

This method allows for the formation of suitable vehicles according to the invention. As polymer base also mixtures of proteins and carbohydrates can be used in this process.

In this way vehicles are formed that are stable and can be used in the various applications according to the invention. The Examples below show many different embodiments for the formation of the vehicles according to the invention. The vehicles will not gelate again when solved, even not when heated or boiled, and, as is shown in the Examples they do not spontaneous fall apart which would cause untidy release of any active component.

The size of the vehicles depends on the breaking and grinding process. Breaking is preferably done by pressing the gel through a sieve of a desired mesh size. If necessary, finer particles can be formed by additional grinding the sieved particles. The size of the vehicles preferably can range from 0.5 µm to 100 µm and the optimal size will depend on the specific application for which they are used. It is generally thought that small vehicles are preferable for therapeutic applications, where the vehicles need to taken up by the body or are injected. Large vehicles can be used preferably, e.g. for flocculation of charged particles (such as bacteria) from a solution.

It is thought that loading of the active component is possible because complexes are formed due to electrostatic interactions between the charged groups of the cross-linked polymer and the charged groups on the compound of interest. In the case that neutral components and/or polymers are use complex formation will probably be caused by hydrostatic interactions between hydrophobic groups.

The active component can be of any size and weight, as long as the vehicles can accommodate stable complexing with said compound, but it will preferably have a weight of less than 50 kD, more preferably less than 30 kD and most preferably less than 10 kD.

The active component which is available in the vehicle will not be released unless an external stimulus changes the property of the vehicle This has the advantage that the active component is not spilled to the environment or—in case of pharmaceutical and/or nutraceutical carriers—to parts of the body where it is not wanted, or even toxic. The stimulus can be of any origin, as long as it is able to open up the vehicle or reduce the complexation of the active ingredient with the vehicle so that the active component will be released. Basically there are two kinds of stimuli that can be employed, namely through electrostatic interaction between the vehicle and active ingredient or through hydrolysis of the polymers.

Electrostatic interaction effects can be accomplished through changes in pH, salt concentration or other general mechanisms. Generally this will result in the exchange of the active component with the free ions of the solution. Hydrolysis of the polymer chains can be accomplished via the action of acids or bases or, preferably, enzymes.

In a preferable embodiment, the invention encompasses vehicles in which the external stimulus which is able to trigger the vehicle to decompose is an enzyme which is able to degrade the polymer. A large number of enzymes which can convert the above mentioned polymers whereupon the embedded active component is released, are known, such as amylase, hemicellulase, xylanase, glucanase, pullulanase, arabinodase, cellulase, pectinase, mannanase or peptidase or protease.

One of the main classes which can be used as active component in the vehicles of the invention are antimicrobial substances. The following compounds can be preferably used as antimicrobial substances: bacteriocins, such as nisin and pediocin; metals or derived metals, such as metal oxides, metal salts, metal complexes or alloys; antibiotics, such as penicillin, erythromycin, ampicillin, isoniazid, tetracycline, sulphonamides and chloramphenicol; vegetable toxins, such as defensins, lectins, and anti-fungal proteins; ethanol; $H_2O_2$-producing enzymes such as oxidases; organic acids such as propionic acid and derived propionates, sorbic acid and derived sorbates, benzoic acid and derived benzoates, lactic acid; sodium diacetate; sodium nitrite; lysozyms and antimicrobial substances from spices.

In embodiments wherein the encapsulated antimicrobial component is administered to the human body, which is preferably done through the oral route, preferably antimicrobial substances are used which are qualified as "foodgrade" by the food and drug administration. Such antimicrobial substances can, for instance, be obtained from herbs and/or spices. Antimicrobial substances (e.g. defensins) produced by plants for defense against bacterial or fungous infections are also usable. Finally, mention should be made of the category of antimicrobial substances produced by fungi which are already being incorporated into the food (e.g. in the preparation of cheese).

Active components can, alternatively, be chosen from various groups of components such as pharmaceutical and/or nutraceutically active compounds, odorants, flavoring compounds, seasoning compounds, etc.

Pharmaceutical and/or nutraceutical active compounds preferably are chosen from compounds which need to be administered in the close vicinity of the cell or organ where they should have their pharmaceutical and/or nutraceutical effect, and which, when given systemically would yield unwanted or even toxic side effects. One group of such compounds are antibiotic compounds, such as the above discussed antimicrobials, where the application needs to be local, e.g. in the mouth (anti-caries). Another group of compounds which would be very well suited for being delivered by the vehicles of the invention are cytostatic compounds, for use in anti-cancer medication. The external stimulus which could trigger the release of compounds in this case, could for instance be the pH, since it is known that the pH in tumours is lower than in the rest of the body (about 6.8-7.0 in tumours and 7.2-7.3 in blood). It lies well within the skill of the person in the art to produce vehicles which would remain stable at normal body pH, but which would be starting the release active components (in this case the cytostatic compound) if a lower pH is encountered.

The advantage of delivery of pharmaceutical and/or nutraceutically active components through the vehicles of the invention is not only an intact delivery and release only by an external stimulus but also the side-effect that the active compound is preserved by the vehicle and will not be metabolized and/or degraded in the body. Furthermore, most of the polymers that can be used for the production of the vehicles are not toxic, and even are foodgrade ingredients.

Especially, the advantage of the present invention is that delivery of nutraceutically active components through the use of vehicles results in passage through the stomach of acid labile components in an intact form, which are released in e.g. the large intestine through the action of enzymes released by the intestinal flora.

It is also possible, according to the present invention, to provide two or more active components. This can be achieved by mixing vehicles loaded with different components or by providing a loading solution with two or more active components solved therein for loading the vehicles (i.e. performing step (i) of the method described above).

The advantage of the present invention is that the active substance will only be released at the location where microorganisms or specific enzyme mixtures are present and active. This means that, in the absence of e.g. microorganisms or active eukaryotic cells, no migration of the antimicrobial substance to the outside will occur, and also that, in the presence of microorganisms to be controlled, the amount of released antimicrobial substance will be limited to a minimum.

A further example is the release of medicines in the intestines where the vehicles can be decomposed by the intestinal enzymes or flora present and thus effect the release of an active substance. For this use, any therapeutically active substance can be used and the invention is not limited to antimicrobial agents. Preferably, those therapeutically active substances are used that run the risk of being decomposed in the mouth, esophagus or stomach. Thus, the vehicles of the invention can also be used for passage through the stomach of an acid- or protease-labile medicine or nutraceutical in the active form.

In addition, a vehicle comprising an antimicrobial substance according to the invention can also very well be used in an anti acne gel. Here again, the advantage compared to the known anti acne agents is that the antimicrobial substance is only released at the moment and at the location where the microorganisms are present. This prevents undesired exposure of the skin to the antimicrobial agent. In addition to use in anti acne agents, the vehicle comprising the antimicrobial substance according to the invention can also be used in other cosmetics. This is because it is known that cosmetics applied on the skin (e.g. creams, lotions, powders, and the like) are a food source for microorganisms. So, infections of microorganisms which use these applied cosmetics as a food source can be prevented by the invention. Thus, the invention also makes it possible for antimicrobial agents used in the current cosmetics (e.g. alcohol or alcohol derivates) to be left out of the cosmetics composition. This is especially advantageous because these agents often cause irritation of the skin. This skin irritation is absent if the vehicle with antimicrobial substance according to the invention is used.

Another application is the use of a vehicle comprising an antimicrobial substance according to the invention in dressing means, such as dressings for wounds, but also sanitary dressings. In wound healing, control of microorganisms is a prerequisite and a dressing according to the invention contributes to the antimicrobial substance being released only at locations where this is needed, and needless exposure of wound tissue to antimicrobial agents being prevented.

Other uses of antimicrobials packaged in a vehicle according to the invention which can be decomposed by microorganisms are possible. Such an antimicrobial substance, in particular a fungicidal substance, can very well be used in fungicidal or anti-fouling paints. The advantage compared to other fungicidal or anti-fouling paints is that the paints according to the invention remain active much longer, since the antimicrobial (fungicidal, anti-fouling) substance is only released when there is reason to.

In addition, a coating comprising vehicles with an antimicrobial substance according to the invention can very well be used in vulnerable systems. In this context, vulnerable systems are systems (materials, humid environments) susceptible to infection by microorganisms, such as (the cut stems of) cut flowers, plant roots, nutrient media of rock wool or other material, etc. Coating this type of materials using a coating according to the invention does not hinder the functions (e.g. water or nutrient intake) of the materials, but still provides a sufficient protection against microorganisms.

Further, a coating according to the invention could also very well be used on surfaces which often come into contact with foods and can, in this manner, be a source of contamination. Examples of these are chopping boards for cutting meat, vegetables and the like, work tops or other surfaces on which foods are prepared or put aside, conveyor belts in industrial food preparation and processing, and storage means (racks, crates and the like) where foods are stored without protection. To guarantee sufficient antimicrobial capacity, the coatings have to be applied again after a certain period of time. To determine this moment, the coating can simply be tested by applying a microorganism thereon on purpose and determining whether the coating still contains sufficient vehicles with antimicrobial agent to stop the growth of the microorganism.

Coatings according to the invention can also be used to coat seeds for protection against attack by micro-organisms or to coat air ventilation filters. Seeds are often provided with coatings to provide nutrients for the sprouting seedlings in the first days after sprouting. This, however, is also a period when the seedlings are very vulnerable to infection by micro-organisms. A coating which comprises vehicles according to the invention which are degradable by said micro-organisms upon which degradation an antimicrobial active component would be released would protect seedlings against such infection. It is also possible to apply seed coatings which are degradable by amylase, which is an enzyme which is produced by the sprouts themselves. In this way the antimicrobial substance (or any other active component, such as a deterrent) will be released at the moment that the seeds are sprouting and will thus protect the fresh sprouts. Coatings on air ventilation filters are known to collect a vast amount of micro-organisms. Sometimes the environmental conditions in or on such a filter are favorable for the generation of colonies of such micro-organisms, which, in turn, will clot the filter and make the filter inoperable. It will be clear that a coating with vehicles according to the invention, wherein such vehicles comprise an antimicrobial substance, will prevent or inhibit formation of micro-organism colonies and thus increase the lifetime of such an air ventilation filter.

Vehicles according to the invention can also be used for addition to edible substances. Preferably the vehicles will be degradable by amylase, which is abundant in the mouth due to the presence of saliva. Such vehicles could contain active components which would be useful for dental applications, such as fluoride compositions and/or anti-caries compounds. Examples of such compounds are sodium fluoride or fluoride complexing agents.

In another preferred embodiment of the invention such vehicles would comprise flavoring compounds, such as would be normally present in food or in dental care compounds. When used in foodstuffs, the application of the vehicles of the invention would provide a new taste sensation, wherein the flavoring compound is only released when the vehicles come into contact with the amylase in saliva. Thus, use of the vehicles in such a way could cause a slow change of taste of a foodstuff in the mouth.

In another preferred embodiment of the invention such vehicles would comprise active components such as iron or bitter tasting drugs or nutraceuticals. When used in foodstuffs, the application of the vehicles of the invention results in masking of the undesired flavour. Use of the vehicles in such a way does not result in release of the active component in the mouth, but release can be triggered by the low pH in the stomach or by enzymes other than amylase in the stomach or small or large intestine.

Another embodiment of the invention is use of the unloaded vehicles (i.e. not or not yet comprising an active component) for immobilization or isolation of specific substances in a solution. This can for instance be done on basis of charge or on basis of size. If a solution contains two components which differ by charge or by size, it is possible to add vesicles according to the invention which will be loaded by only one of those components and which can be easily harvested, e.g. by mild centrifugation. The compound caught in the vehicles can then again be released by applying the external stimulus (e.g. pH or an enzyme) which causes release of the component. A difference in charge would mean that positively charged vehicles can catch negatively charged compounds from a solution and vice-versa. To catch compounds of a specific size it would be possible to devise vehicles, which, on basis of their three-dimensional structure, would only allow uptake of compounds to a specific size limit.

Immobilization of compounds in a solution can be performed on basis of charge. If relatively large, charged vehicles will be added to a solution which holds an oppositely charged compound, the vehicle will either take up this compound (if the size limit of the vehicle would be appropriate) or it will bind electrostatically to the vehicle. If the vehicles are large enough they will precipitate either by themselves or with light centrifugation, thereby also precipitating the bound component. If the particles in the solution are both large and charged (e.g bacteria), then the vehicles can be relatively light and still be able to form a precipitate. This, because many of the vehicles will electrostatically bind to the particle in solution, thereby increasing its mass and decreasing its solubility enormously. The vehicles of the invention are thus perfectly suited to precipitate bacteria, esp. gram-negative bacteria.

Preparation and use of the vehicles of the invention will be shown in the Examples. A person skilled in the art will understand that the invention is not limited to the specific embodiments and uses mentioned, but that the invention can be manifested in various other embodiments which will be readily available to said person.

EXAMPLES

Example 1

Synthesis of Gel A

A solution of 54 mg of NaOH in 90 mL of water was brought to a temperature of 0° C. To this, 600 µl of divinyl sulphone (DVS) were added. Then, 15 grams C6-oxidized starch having a degree of oxidation (DO) of more than 90% was added slowly with vigorous stirring. The solution changed overnight into a soft and virtually colorless transparent gel. This gel was pressed through a sieve with meshes of approximately 1 mm$^2$, after which 1 liter of water was stirred through the gel, which water was absorbed directly. After this, the gel was precipitated using 2 liters of ethanol and was then washed twice using ethanol and once using acetone, after which the gel was air-dried. This resulted in 12.1 grams of gel having a free swelling (net weight divided by dry weight) of 59 in water.

Example 2

Synthesis of Gel B

Synthesis and further processing as gel A, but using C6-oxidized starch having a DO of 50% instead of more than 90%. This resulted in 9.78 g of gel having a free swelling of 51 in water.

Example 3

Synthesis of Gel C

To 89 mL of ice water, 1.00 mL of a NaOH solution, obtained by dissolving 539 mg of NaOH with 10.1 mL of water, was added. To this, 800 µl of DVS were added. Then, 10 grams of C6-oxidized starch (DO 30%) were added slowly with vigorous stirring. The solution changed overnight into a hard and virtually colorless transparent gel. This gel was pressed through a sieve with meshes of approximately 1 mm$^2$, after which 0.5 liter of water was stirred through the gel, which water was absorbed directly. After this, the gel was precipitated using 1 liter of ethanol, and then washed twice using ethanol and once using acetone, after which the gel was air-dried. This resulted in 9.02 grams of gel having a free swelling (net weight divided by dry weight) of 49 in water.

Example 4

Synthesis of Gel D

To a solution of 58 mg of NaOH in 90 mL of ice water, 600 µl of DVS were added. Fifteen grams of C6-oxidized starch (DO 30%) were added slowly with vigorous stirring. The solution changed overnight into a hard and virtually colorless transparent gel. This gel was pressed through a sieve with meshes of approximately 1 mm$^2$, after which 0.5 liter of water was stirred through the gel, which water was absorbed directly. After this, the gel was precipitated using 1 liter of ethanol, and then washed twice using ethanol and once using acetone, after which the gel was air-dried. This resulted in 13.4 grams of gel having a free swelling of 51 in water.

Example 5

Synthesis of Gel E

A solution of 58 mg of NaOH in 90 mL of water was cooled to a temperature of 0° C. To this, 400 µl of DVS were added. Directly after this, a mixture of 10.0 grams of Paselli SA 2 and 5.0 grams of the Na salt of carboxymethyl cellulose (having a low viscosity) were added with vigorous stirring. The solution changed overnight into a soft, milk white gel. This gel was pressed through a sieve with meshes of approximately 1 mm², after which 0.5 liter of water was stirred through the gel, which water was absorbed directly.

After this, the gel was precipitated using 1 liter of ethanol, and then washed twice using ethanol and once using acetone, after which the gel was air-dried. This resulted in 9.66 grams of gel having a free swelling of 31 in water.

Example 6

Synthesis of Gel F

To a solution of 2.4 grams NaOH in 480 mL water 120 g Paselli SA 2 was added. When the Paselli SA 2 was completely dissolved 73 mL of glycidyltrimethylammonium chloride (70% in water) was added and the reaction mixture was stirred at 60° C. for 120 minutes. After cooling down to room temperature 1 g NaOH (dissolved with 2 mL water) was added to 100 mL of the obtained reaction mixture. Then 3 mL epichlorohydrin was added and the reaction mixture was stirred for 15 min. This solution was stored for three days at 37° C. After cooling to room temperature the gel was pressed through a sieve (1 mm² meshes), and washed 10 times with 1 liter water, 3 times with 1 liter ethanol, 3 times with acetone and the resulting precipitate was dried on air. This gave 18.05 grams gel with a free swelling of 58 in water.

Example 7

Synthesis of Gel G

Synthesis and further processing as described for gel F, but using 2 mL of glycerol diglycidylether instead of epichlorohydrin. This resulted in 16.45 grams of gel having a free swelling of 32 in water.

Example 8

Synthesis of Gel H

To a solution of 1 gram NaOH in 90 mL water under vigorous stirring 15 grams 30% C6-oxidized starch was added. After dissolving 2 mL epichlorohydrin and storing the reaction mixture for 3 days at 37° C. the resulting gel was pressed through a sieve (1 mm² meshes). The gel particles were washed 10 times with 1 liter water, 3 times with 1 liter ethanol, 3 times with acetone and dried on air. The yield was 7.21 grams dry gel with a free swelling capacity of 134 in water.

Example 9

Synthesis of Gel I

Synthesis and further processing as described for gel H, but using 0.9 mL of glycerol diglycidylether instead of epichlorohydrin. This resulted in 8.22 grams of gel having a free swelling of 143 in water.

Example 10

Synthesis of Gel J

In 90 mL water 1 g NaOH and 12 grams carboxymethyl cellulose low viscosity, sigma) was dissolved. Then 2 mL epichlorohydrin was added and after 15 min. stirring at room temperature the solution was stored at 37° C. for three days. After cooling to room temperature the gel was pressed through a sieve (1 mm² meshes), and washed 10 times with 1 liter water, 3 times with 1 liter ethanol, 3 times with acetone and dried on air. This gave 5.64 grams gel with a free swelling of 38 in water.

Example 11

Synthesis of Gel K

In 90 mL water 0.5 g NaOH and 10 grams carboxymethyl cellulose (low viscosity, sigma) was dissolved. Then 0.5 mL glycerol diglycidylether was added and after 15 min. stirring at room temperature the solution was stored at 37° C. for three days. After cooling to room temperature the gel was pressed through a sieve (1 mm² meshes), and washed 10 times with 1 liter water, 3 times with 1 liter ethanol, 3 times with acetone and dried on air. This gave 13.65 grams gel with a free swelling of 180 in water.

Example 12

Synthesis of Gel L

In 720 mL water 4 grams NaOH and 96 grams Paselli SA 2 was dissolved. Then 16 mL glycerol diglycidylether was added, and the reaction mixture was stirred for 15 minutes at room temperature. The solution was stored at 37° C. for three days. After cooling to room temperature the transparent gel was pressed through a sieve (1 mm² meshes), and washed 4 times with 5 liter water, 3 times with 1 liter ethanol, 3 times with acetone and dried on air. The yield was 71.98 grams dry gel with a free swelling of 22 in water.

Example 13

Synthesis of Gel M

In 720 mL water 8 grams NaOH and 96 grams Paselli SA 2 was dissolved. Then 16 mL epichlorohydrin was added, and the reaction mixture was stirred for 15 minutes at room temperature. The solution was stored at 37° C. for two days. After cooling to room temperature the transparent gel was pressed through a sieve (1 mm² meshes), and suspended in 10 liter water.

After one night sedimentation at room temperature the solution was removed by decantation, resulting in about one liter wet gel. The gel was precipitated by addition of three liter ethanol and washed three times with ethanol and three times with acetone and dried on air. This gave 52.65 grams of dry gel with a free swelling of 24 in water.

Example 14

Synthesis of Gel N

To a solution of 1.2 grams NaOH and 60 grams Paselli SA 2 in 240 mL water 73 mL glycidyltrimethylammonium chloride was added. Then the reaction mixture was stirred at 60° C. for 2 hours. After cooling to room temperature, 100 mL of the resulting reaction mixture was added to a solution of 3.5 grams NaOH and 35 grams carboxymethylcellulose (low viscosity, sigma) in 220 mL water. To this mixture 8 mL epichlorohydrin was added. The reaction mixture was stirred at room temperature for 15 minutes and subsequent stored at 37° C. for three days. After cooling to room temperature the transparent gel was pressed through a sieve (1 mm² meshes), and washed 10 times with 1 liter water, 3 times with 1 liter ethanol, 3 times with acetone and dried on air. The yield was 42.62 grams of dry gel with a free swelling capacity of 9.4 in water.

Example 15

Synthesis of Gel O

To a solution of 1.5 grams NaOH in 160 mL water 15 grams carboxymethyl cellulose and subsequent 2.5 mL epichlorohydrin was added. After stirring for 15 minutes at room temperature the solution was stored for three days at 37° C. After cooling to room temperature the tough and transparent gel was cut into pieces of about 1 cm$^3$ and added to 3 liter water. The gel pieces were stored for one night at room temperature whereby almost all water was absorbed. The transparent and brittle gel pieces were pressed through a sieve (1 mm$^2$ meshes), and washed 10 times with 1 liter water, 3 times with 1 liter ethanol, 3 times with acetone and dried on air. This gave 9.8 grams of dry gel with a free swelling of 228 in water.

Example 16

Synthesis of Gel P

To a solution of 6 grams NaOH and 150 grams Paselli SA 2 in 300 mL water 375 mL glycidyltrimethylammonium chloride was added. Then the reaction mixture was stirred at 70° C. for 2 hours. After cooling to 4° C., 670 mL of the resulting reaction mixture was added to a solution of 15 grams carboxymethylcellulose (low viscosity, sigma) and 80 grams dextran (molecular weight 500 KD, Pharmacia) and 200 mL ice in 800 mL water. After the addition of 9 mL divinyl sulphone the solution was stored at room temperature for three days. The gel was pressed through a sieve and washed 10 times with water. Then the gel was washed three times with ethanol and three times with acetone and dried on air. This resulted in 72 grams dry gel with a free swelling of 163 in water.

Example 17

Synthesis of Gel Q

In 2.7 liter water 1.69 grams NaOH and 300 grams carboxymethyl cellulose (low viscosity, sigma) was dissolved. After cooling to 4° C. 11 mL divinyl sulphone was added. The solution was stored at room temperature for three days. The resulting gel was pressed through a sieve and washed 10 times with water and three times with ethanol and dried on air. The yield was 242 grams dry gel with a free swelling capacity of 55 in water.

Example 18

Synthesis of Gel R

To a solution of 2.4 grams NaOH and 60 grams Paselli SA 2 in 240 mL water 146 mL glycidyltrimethylammonium chloride was added. Then the reaction mixture was stirred at 70° C. for 4 hours. After cooling to 4° C. 300 mL of the resulting reaction mixture was added to a solution of 10 grams C6-oxidized starch (DO 30%) and 20 grams dextran (molecular weight 500 KD, Pharmacia) in 200 mL water. After cooling the solution in an ice-bath 3 mL divinyl sulphone was added. Then the solution was stored at room temperature for three days. The resulting gel was pressed through a sieve (1 mm$^2$ meshes) and suspended in 1 liter water. Under vigorous stirring 1.5 liter acetone was added. This resulted in contraction of the gel. After 2 hours of sedimentation 1.3 liter solution could be decanted. After the addition of 0.5 liter acetone the gel precipitated and was washed three times with acetone and dried on air. This resulted in 104 grams dry gel with a free swelling of 47 in water.

Example 19

Synthesis of Partially Hydrolyzed Guar Gum

A solution of 10 mL 87% H$_2$SO$_4$ in 1 liter water was heated to 50° C. Then under vigorous stirring 50 grams guar gum was added as fast as possible. The very viscous reaction mixture was stirred slowly for 15 minutes which resulted in a lower viscosity. Then the temperature was raised to 60° C., and kept at a temperature between 60° C. and 70° C. during 1.5 hours. Hereafter 60 grams sodium acetate was added and the reaction mixture was stirred at a temperature of 85° C. during 30 minutes. After cooling to room temperature the cloudy solution was centrifuged at 3500 G. To the clear supernatant 2 liter ethanol was added. The precipitate was isolated using a glass filter with pore size 2 and suspended in 0.5 liter water/ethanol (4/6). The precipitate was isolated on a glass filter and washed three times with ethanol and three times with acetone and dried on air. The yield was 37.57 grams partially hydrolyzed guar gum.

Example 20

Synthesis of Gel S

To a solution of 2.4 grams NaOH and 60 grams Paselli SA 2 in 240 mL water 146 mL glycidyltrimethylammonium chloride was added. Then the reaction mixture was stirred at 70° C. for 2 hours. After cooling to 4° C. 40 mL of the resulting reaction mixture was added to a solution of 5 grams partially hydrolyzed guar gum in 50 mL water. To the reaction mixture 400 µL divinyl sulphone was added. The solution was stored at room temperature for three days. Then the resulting gel was pressed through a sieve (1 mm$^2$ meshes), and suspended in 0.5 liter water. The gel was precipitated by the addition of 1 liter ethanol and washed three times with ethanol and two times with acetone and dried on air. The yield was 8.8 grams of gel with a free swelling of 67 in water.

Example 21

Synthesis of Gel T

To a solution of 50 mg NaOH in 90 mL water/ice 5 grams partially hydrolyzed guar gum and 5 grams carboxymethyl cellulose (low viscosity, sigma) was added. After dissolving 400 µL divinyl sulphone the reaction mixture was stored at room temperature for three days. Then the resulting gel was pressed through a sieve (1 mm$^2$ meshes), and suspended in 0.5 liter water. The gel was precipitated by the addition of 1 liter ethanol and washed two times with ethanol and two times with acetone and dried on air. The yield was 8.7 grams of gel with a free swelling of 29 in water.

Example 22

Synthesis of Gel U

In 180 mL water/ice 100 mg NaOH, 10 grams dextran (molecular weight 500 KD, Pharmacia) and 10 grams carboxymethyl cellulose (low viscosity, Sigma) was dissolved. Then 800 µL divinyl sulphone was added. The solution was stored at room temperature for three days. The gel was isolated as described for gel T. This gave 18.21 grams gel with a free swelling capacity of 87 in water.

Example 23

Synthesis of Gel V

To a solution of 2.4 grams NaOH and 60 grams Paselli SA 2 in 240 mL water 146 mL glycidyltrimethylammonium chloride was added. Then the reaction mixture was stirred at 70° C. for 2 hours. After cooling to 4° C. 70 mL of the resulting reaction mixture was added to a solution of 10 grams dextran (molecular weight 500 KD, Pharmacia) in 90 mL water. Then 1000 µL divinyl sulphone was added. The solution was stored at room temperature for three days and the resulting gel was pressed through a sieve (1 $mm^2$ meshes), and suspended in 1 liter water. After precipitation with 2 liter ethanol the gel was suspended in 2 liter water and precipitated by addition of 4 liter acetone. The precipitate was suspended in 2 liter water, precipitated by addition of 4 liter acetone and washed three times with acetone and dried on air. The yield was 19.92 grams dry gel with a free swelling of 103 in water.

Example 24

Synthesis of Gel W

To a solution of 55 mg NaOH in 90 mL water/ice 10 grams dextran (molecular weight 500 KD, Pharmacia) was added, followed by 600 µL divinyl sulphone. The solution was stored at room temperature for three days. The resulting gel was pressed through a sieve (1 $mm^2$ meshes) suspended in 0.5 liter water, and precipitated by the addition of 0.5 liter ethanol. Then the precipitate was again suspended in 0.5 liter water and precipitated by the addition of 0.5 liter ethanol. Finally, the precipitate was washed four times with ethanol and dried on air. This gave 13.08 grams with a free swelling of 8.5 in water.

Example 25

Synthesis of Gel X

To a solution of 2.4 grams NaOH and 60 grams Paselli SA 2 in 240 mL water 146 mL glycidyltrimethylammonium chloride was added. Then the reaction mixture was stirred at 70° C. for 2 hours. After cooling to 4° C., to 90 mL of the resulting reaction mixture 600 µL divinyl sulphone was added. The resulting gel was pressed through a sieve (1 $mm^2$ meshes) suspended in 0.5 liter water, and precipitated by the addition of 2 liter ethanol. Then the precipitate was suspended in 0.5 liter water and precipitated by the addition of 4 liter ethanol. The precipitate was washed three times with ethanol and dried on air. This resulted in 7.26 grams of gel with a free swelling of 56 in water.

Example 26

Synthesis of Gel Y

To a solution of 55 mg NaOH in 90 mL water/ice 10 gram partially hydrolyzed guar gum was added. After the addition of 800 µL divinyl sulphone the solution was stored at room temperature for three days. The resulting gel was pressed through a sieve (1 $mm^2$ meshes) suspended in 0.5 liter water, and precipitated by the addition of 1 liter ethanol. The precipitate was washed two times with ethanol and two times with acetone and dried on air. The yield was 8.63 gram gel with a free swelling of 11 in water.

Example 27

Synthesis of Gel Z

In 150 mL water 1 gram NaOH and 10 grams C6-oxidized starch (DO 30%) was dissolved. After heating to 45° C. 4 grams sodium trimetaphosphate was added and the temperature was kept this value for 2 hours. During the first minutes the reaction mixture was stirred. After this time the viscosity became very high. The gel was stored at room temperature for one day and then pressed through a sieve (1 $mm^2$ meshes) and suspended in 1 liter water. Then the gel was precipitated by the addition of 1.5 liter ethanol and washed two times with ethanol and one time with acetone and dried on air. This gave 6.63 grams dry gel with a free swelling of 138 in water.

Example 28

Synthesis of Gel BA

In 3750 mL water/ice 400 grams Paselli SA 2 and 2 grams NaOH was dissolved. After the addition of 20 mL divinyl sulphone the solution was stored at room temperature for three days. The gel was pressed through a sieve and suspended in water to a final volume of 40 liter. After 4 hour sedimentation about 25 liter of the resulting solution was decanted. To the remaining wet gel 15 liter ethanol was added. The precipitate was washed three times with ethanol and three times with acetone and dried on air. The yield was 342.86 grams of dry gel with a free swelling of 9.8 in water.

Example 29

Synthesis of Gel BB

In a solution of 0.53 grams NaOH in 750 mL water 40 grams Paselli SA 2 and 40 grams C6-oxidized starch (DO 30%) was dissolved. The solution was cooled in an ice-bath. After addition of 20 mL divinyl sulphone the solution was stored at room temperature for three days. The resulting gel was pressed through a sieve (1 $mm^2$ meshes) suspended in 1 liter water, and precipitated by the addition of 2 liter ethanol. Then the precipitate was suspended in 2 liter water and precipitated again by the addition of 2 liter ethanol. Finally, the gel was washed two times with ethanol and two times with acetone and dried on air. This resulted in 69.03 grams of gel with a free swelling capacity of 25 in water.

Example 30

Synthesis of Gel BC

To a solution of 1.2 grams NaOH and 30 grams Paselli SA 2 in 120 mL water 37 mL glycidyltrimethylammonium chloride was added. Then the reaction mixture was stirred at 70° C. for 2 hours. After cooling to 4° C. 70 mL of the resulting reaction mixture was added to a solution of 10 grams C6-oxidized starch (DO 30%) in 90 mL water. Then 1000 µL divinyl sulphone was added and the solution was stored at room temperature for three days. The resulting gel was pressed through a sieve (1 $mm^2$ meshes) and suspended in 1 liter water. The gel was precipitated by the addition of 1.5 liter ethanol and 4 liter acetone and washed three times with acetone and dried on air. The yield was 22.87 grams gel with a free swelling of 16 in water.

Example 31

Synthesis of Gel BD

Cationic starch was prepared from Paselli SA 2 as described for gel BC using 73 mL glycidyltrimethylammonium chloride instead of 37 mL. After cooling to 5° C. 70 mL of the resulting solution was added to a solution of 10 grams Paselli SA 2 in 90 mL water. Subsequent 1000 µL divinyl sulphone was added. The solution was stored at room temperature for three days. Then resulting gel was pressed through a sieve (1 mm² meshes) and suspended in 1 liter water. The gel was precipitated by addition of 2 liter acetone and three times washed with acetone and dried on air. This gave 13.90 grams dry gel with a free swelling of 40 in water.

Example 32

Synthesis of Gel BE

A solution of 3 grams NaOH, 10 grams Paselli SA 2 and 8 grams sodium trimethaphosphate was kept at a temperature of 45° C. for 2 hours. Then the resulting gel was immediately pressed through a sieve (1 mm² meshes), suspended in 1 liter water and precipitated by the addition of 1 liter ethanol. The precipitate was suspended with 1 liter water, precipitated using 1 liter ethanol and washed two times with ethanol and one time with acetone and dried on air. The yield was 7.12 grams of gel with a free swelling of 103 in water.

Example 33

Synthesis of Gel BF

In 90 mL water 10 grams C6-oxidized starch (DO 90%), 5 grams Paselli SA 2, 4 grams sodium trimetaphosphate and 1 gram NaOH was added. The solution was kept at a temperature of 45° C. for 2 hours. During the first 8 minutes the solution was stirred. After this time the viscosity became very high. The gel was stored for three days at room temperature. The gel was isolated as described for gel BE. This resulted in 6.48 grams with a free swelling capacity of 69 in water.

Example 34

Synthesis of Gel BG

Synthesis and isolation as described for gel BF, but using 5 grams C6-oxidized starch (DO 30%) and 5 grams C6-oxidized starch (DO 90%) as the only carbohydrates. The yield was 8.34 grams gel with a free swelling of 77 in water.

Example 35

Synthesis of Gel BH

A suspension of 20 grams waxy maize starch in 400 mL water was heated to a temperature of 80° C. and after pasting of the starch cooled down to 40° C. Then 16 grams sodium trimetaphosphate and 4 grams NaOH was added. After keeping the temperature at 40° C. for 0.5 hour the reaction mixture was cooled down to room temperature. The gel was isolated as described for gel BF, but after 1 day storing at room temperature instead of three days. This resulted in 17.95 grams dry gel with a swelling capacity of 25 in water.

Example 36

Synthesis of Gel BI

In 90 mL water 1 gram NaOH, 15 grams C6-oxidized starch (DO more than 90%) and 6 grams sodium trimetaphosphate was dissolved. The solution was heated to 40° C. and kept at this temperature for 2 hours. During the first 10 minutes the solution was stirred. After this time the viscosity became very high. Then gel was stored at room temperature for three days, pressed through a sieve (1 mm² meshes) and suspended in 1 liter water. The gel was precipitated by addition of 2 liter ethanol and two times washed with ethanol and one time with acetone and dried on air. This gave 17.69 gram dry gel with a free swelling of 25 in water.

Example 37

Synthesis of Gel BJ

To a solution of 87 grams C6-oxidized starch (DO 30%) and 400 mg NaOH in 740 mL water, which was cooled to 4° C., 3000 µL divinyl sulphone was added. The solution was stored for three days at room temperature. The resulting gel was stored at room temperature for three days, pressed through a sieve (1 mm² meshes) and suspended in 0.5 liter water. Then the gel was precipitated by addition of 2 liter ethanol and one times washed with ethanol and two times with acetone and dried on air. The yield was 80.71 grams dry gel with a free swelling capacity of 156 in water.

Example 38

Synthesis of Gel BK

To a solution of 54 mg NaOH and 800 µL divinyl sulphone, which was cooled to 0° C., 5 grams Paselli SA 2 and 5 grams carboxymethyl cellulose (medium viscosity, Sigma) was added under vigorous stirring. The solution was stored at room temperature for three days. The gel was isolated as described for gel BI. This gave 6.51 grams dry gel with a free swelling of 150 in water.

Example 39

Synthesis of Gel BL

The gel was synthesized and isolated as described for gel BJ, but using 4000 µL divinyl sulphone instead of 3000 µL. The yield was 81.37 grams gel with a free swelling of 185.

Example 40

Synthesis of Gel BM

To a solution of 2% of sugar beet pectin in 0.1 M acetate buffer pH 5.0, 2.4 U/ml of laccase (Trametes versicolor) was added and incubated at 40° C. for 2 hours. A transparent gel was obtained, which was pressed through a sieve with meshes of approximately 1 mm². Gel particles were precipitated using two volumes of ethanol and was then washed three times with ethanol and three times with acetone, after which the gel particles were air-dried.

Example 41

Incorporating Lysozyme Into Gel BM

To 15 ml of water, 100 mg of the pectin-based gel particles obtained in example 1 were added. Next, 1 ml of a lysozyme solution of 25 mg/ml is added and the solution is stirred for 15 minutes. The gel particles are sedimented by means of centrifugation and a sample of 1 ml was taken from the supernatant and the amount of lysozyme determined based on the fluorescence of the protein (excitation 290 nm, emission 340 nm). After that, again 1 ml of a lysozyme solution of 25 mg/ml is added and the solution is stirred for 15 minutes. The cycle of addition of lysozyme and subsequent taking a sample is repeated 11 times.

Figure 5:
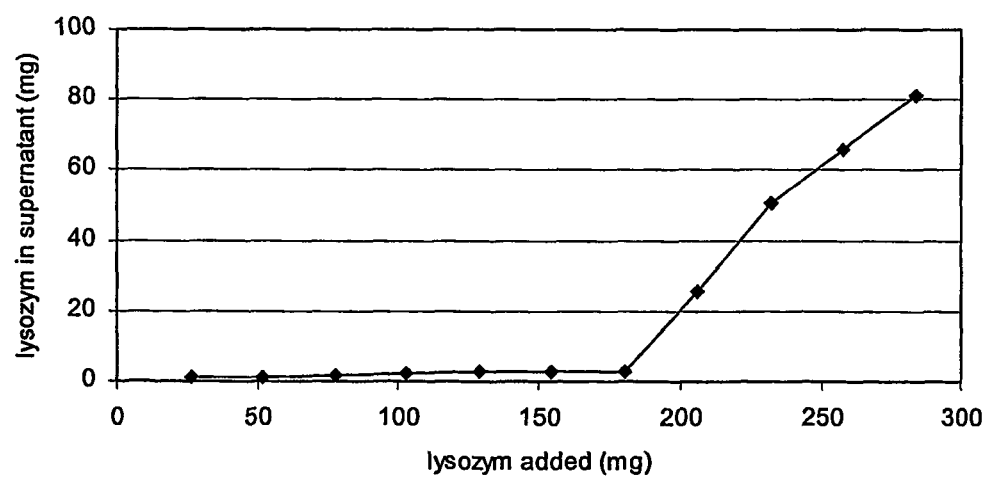
FIG. 5: Incorporation of active component. The graph shows the cumulative amount of lysozyme that is determined in the supernatant, and which is therefore not incorporated into the pectin-based vehicles of Gel A.

The cumulative amount of lysozyme that is determined in the supernatant, and which is therefore not incorporated into the pectin-based vehicle, is depicted in FIG. 5. This shows that when 175 mg of lysozym is added, only 3 mg is found in the supernatant, showing that 172 mg is incorporated into the vehicle. Further additions of lysozyme result in a linear increase in the amount of lysozyme in the supernatant, showing that no additional incorporation occurs. The capacity of the pectin-based vehicle for lysozyme is therefore 1.7 mg lysozym per mg of pectin-based vehicle.

Example 42

Release of Lysozyme from Gel BM

To 15 ml of water, 100 mg of the gel particles obtained in example 1 were added. Next, 3 ml of a lysozyme solution of 25 mg/ml is added and the solution is stirred for 1 minutes. Similar to example 2, this results in incorporation of lysozyme into the pectin-based gel particles for 98%. Next, 200 µl of Pectinase (Sigma, P2611) is added and the solution is incubated for 4 hours at 40° C. at pH 4.5. Analysis of the amount of lysozyme present in the supernatant obtained after centrifugation indicated that 97% was released from the pectin-based vehicle by the action of pectinase.

Example 43

Synthesis of Gel BN 3 grams of gelatin (bloom 300; Sigma P2500) was dissolved in 100 ml of 0.1 M NaAc buffer pH 5.0 by heating the solution to 60° C. The solution was cooled to 40° C. and 250 µl of 1 mg/ml microbial transglutaminase (Ajinomoto) was added and the solution was subsequently incubated for 2 hours. A transparent gel was obtained, which was pressed through a sieve with meshes of approximately 1 mm2. Gel particles were precipitated using two volumes of ethanol and was then washed three times with ethanol and three times with acetone, after which the gel particles were air-dried.

Example 44

Incorporating Glucose Oxidase into Gel BN

To 15 ml of water, 100 mg of the gelatin-based gel particles obtained in example 4 were added. Next, 1 ml of a glucose oxidase solution of 25 mg/ml is added and the solution is stirred for 15 minutes. The gel particles are sedimented by means of centrifugation and a sample of 1 ml was taken from the supernatant and the amount of glucose oxidase determined based on the fluorescence of the protein (excitation 296 nm, emission 340 nm). After that, again 1 ml of a glucose oxidase solution of 25 mg/ml is added and the solution is stirred for 15 minutes. The cycle of addition of glucose oxidase and subsequent taking a sample is repeated 12 times.

Figure 6:
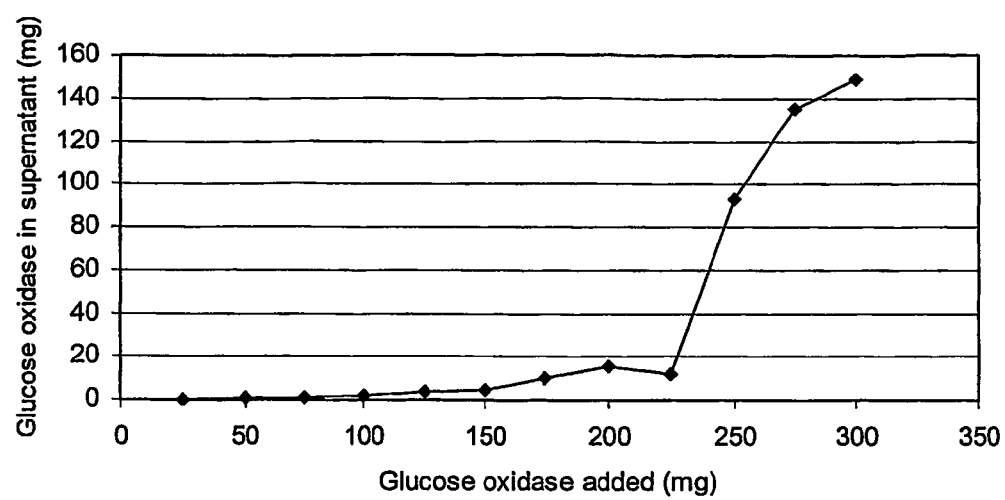
FIG. 6: Incorporation of active component. The graph shows the cumulative amount of glucose oxide that is determined in the supernatant, and which is therefore not incorporated into the pectin-based vehicles of Gel D.

The cumulative amount of glucose oxidase that is determined in the supernatant, and which is therefore not incorporated into the gelatin-based vehicle, is depicted in FIG. 6. This shows that when 100 mg of glucose oxidase is added, only 2 mg is found in the supernatant, showing that 98 mg is incorporated into the gelatin-based vehicle. When 225 mg of glucose oxidase is added, 12 mg is found in the supernatant, indicating that 213 mg is incorporated. Further additions of glucose oxidase result in a strong increase in the amount of glucose oxidase in the supernatant, indicating that no additional incorporation occurs. The capacity of the gelatin-based vehicle for glucose oxidase is therefore approximately 2.2 mg glucose oxidase per mg of gelatin-based vehicle.

Example 45

Synthesis of a Fluorescent Labeled Lysozyme

To 2 ml of a solution of approximately 2.5% lysozyme (g/v) in 10 mM. carbonate buffer pH 9.5, 0.25 ml ruthenium (II)(bipyridil)2phenanthroline-isothiocyanate chloride in acetonitril was added. This solution was stirred for 1 hour. The total reaction volume of 2.25 ml was eluted over a gel-permeation column from BioRad (Econo-Pac 10DG) with a 10 mM. PBS buffer pH6.5. In this way the reaction mixture is cleaned up, as molecular fractions smaller than 6000 daltons are removed and at the same time a buffer exchange is realized.

The collected fraction contains about 1.25% (g/v) of labeled lysozyme and can be stored as such for a couple of weeks or after freeze-drying at 4° C.

Example 46

Release of Ruthenium Labeled Lysozyme from Gel Q

To 10 ml, 50 mg of gel particles obtained in example X were added. Next 0.5 ml of a 1.25% (g/v) solution obtained in example Y is added while mild stirring. The incorporation of the ruthenium labeled lysozyme in the gel particles is complete within 5 minutes. In this example about 50% of the maximum loading capacity of the gel particles is used. The fluorescent lifetime of the labeled lysozym in the CMC gel particles is 1125 nsec. After adding a small amount (100 µl) of celluclose (celluclast from Novozyme) to this suspension the fluorescent labeled lysozyme is slowly released at room temperature as an ion-pair with a large carboxy oligomer as the anion instead of chloride. In an aqueous solution this complex has a fluorescent lifetime of about 1300 nsec. In approximately 30 minutes 90% of all labeled lysozyme is released from the gel particles.

Example 47

Binding Capacity of Three Gels for Two Proteins

To determine the binding capacity of gels C, V and BL for the proteins lysozyme and ovalbumin at neutral pH, 100 mg of a gel was suspended in 15-20 mL water. To these suspensions 1 mL of a protein solution was added.

After stirring the suspension for 5 minutes, and sedimentation of the gel particles for another 5 minutes, a sample of 1 mL has been taken. This was repeated 4 to 22 times. The samples were filtrated using a 0.45 µm filter. Then the concentration of protein was determined by measuring the fluorescence using an excitation wavelength at 290 nm and an emission wavelength of 340 nm. The amount of protein in solution was then compared with the amount of protein added. This is depicted in FIG. 1. If the protein and gel have an opposite charge the first portions of protein will be bound to the gel and the addition of the protein will not result in an increase of the concentration in solution. As soon as the gel is saturated addition of more protein will result in an increase in the concentration of the protein in solution. This point, determined from FIG. 1, will give the capacity. The capacity of the gels C, V and BL for lysozyme appeared to be 1.3, 0.0 and 1.5 gram/gram, respectively. And the capacity of these gels for ovalbumin appeared to be 0.0, 3.8 and 0.0 gram/gram, respectively.

Example 48

Susceptibility of the Different Gels to α-amylase

To 10 ml of water, 50-100 mg of gel were added, after which it was stirred at 37° C. Then, 100 µl of α-amylase were added (Termamyl, Novo Nordisk). The gels C, D and E were found to be dissolved after 1 hour. Gel B was only dissolved after one night and gel A was still not noticeably affected after two days.

Example 49

Incorporating Lysozyme into Gel E and Release Under the Influence of α-amylase

Figure 2:
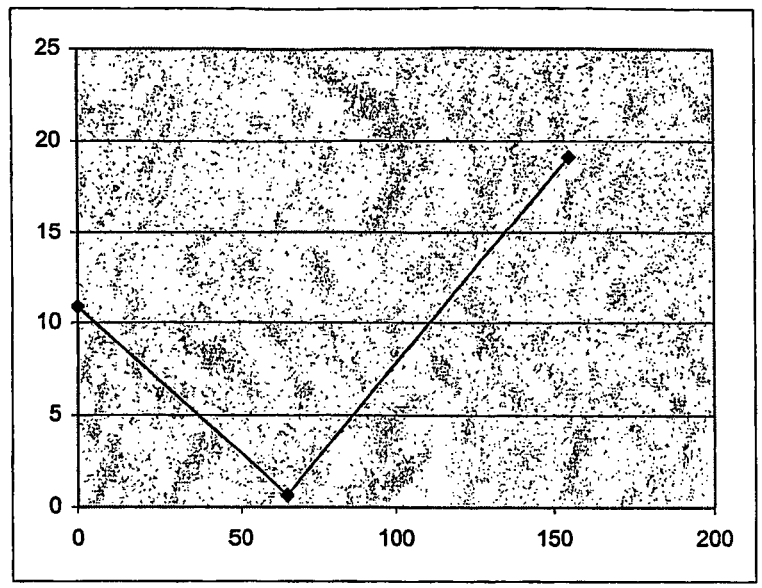
FIG. 2: Gel E. Percentage of free lysozyme (%) as a function of time (minutes).

To a solution of 105 mg of lysozyme in 10 ml of water, 180 mg of gel E were added. After stirring for 10 minutes at room temperature, the gel was washed 6 times using approximately 50 ml of ice water. Each time, the gel was isolated by means of centrifuging (4700 rpm). This resulted in 6.5 grams of gel. Of this gel, 2.9 grams were added to 15 ml of water. Then, it was stirred for 10 minutes at room temperature and for 20 minutes at 37° C. After this, 100 µl of α-amylase were added (Termamyl, Novo Nordisk), after which it was stirred for 1 hour at 37° C. By means of a 0.45-µm filter, a sample was taken for analysis of the solution resulting after deposition of the gel particles 5 minutes after the dry gel was added to the lysozyme solution, minutes after the washed gel containing lysozyme was added to water and after an hour of action of α-amylase. The concentration of lysozyme was determined by measuring the decrease in OD (optical density) in a Micrococcus suspension. The part of the enzyme present which was in solution was found to be, for above samples, 11%, 0.7% and 19% respectively. This is shown in FIG. 2. This means that 89% of the lysozyme was incorporated into the gel by adding the dry gel to a lysozyme solution and that, after the action of α-amylase, the lysozyme concentration had increased by a factor 27.

Example 50

Incorporating Lysozyme into Gel C and Release Under the Influence of α-amylase

Figure 3:
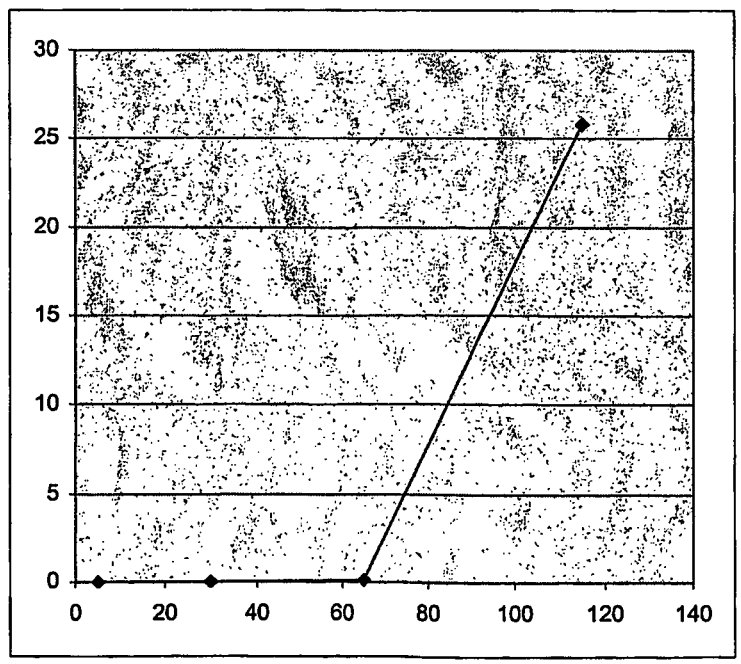
FIG. 3: Gel C. Percentage of free lysozyme (%) as a function of time (minutes).

To a solution of 122 mg of lysozyme in 12 ml of water, 196 ml of gel C were added. After stirring for 5 minutes at room temperature and stirring for 8 minutes at 37° C., the gel was cooled to 0° C., after which the gel was washed 8 times using ice water. This resulted in 6.5 grams of gel. Of this, 4.3 grams were added to 10 ml of water. After stirring for 30 minutes at room temperature and for 35 minutes at 37° C., 100 µl of α-amylase were added (Termamyl, Novo Nordisk), after which it was stirred for 50 minutes at 37° C. After 5, 30, 65 and 115 minutes, a sample was taken for analysis. The part of the lysozyme present that was in solution (in %) is plotted in FIG. 3 as a function of time in minutes. It was found that, after adding gel C, only 0.01% of the lysozyme used was free in solution. After stirring for 30 minutes at room temperature, this was 0.04%, and after again stirring for 35 minutes at 37° C., this was 0.06%. Addition of x-amylase resulted in an increase by a factor 425 in 50 minutes, causing the lysozyme activity to increase to 26% of the amount that was present in the gel.

Example 51

Incorporating Lysozyme into Gel C and Release Under the Influence of α-amylase

Figure 4:
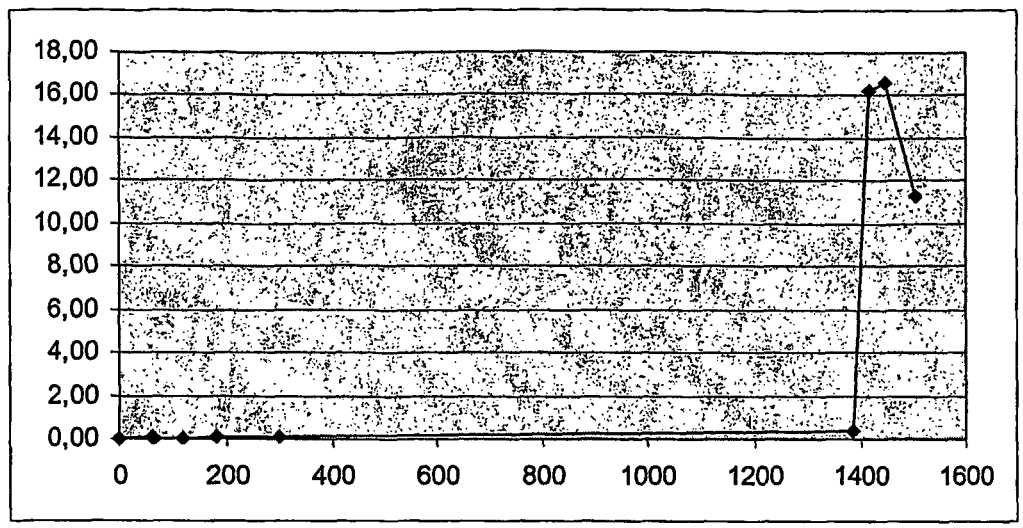
FIG. 4: Gel C. Percentage of free lysozyme (%) as a function of time (minutes).

To a solution of 130 ml of lysozyme in 30 ml of water, 205 mg of gel C were added. After stirring for 10 minutes at room temperature, taking a sample of the solution, and then cooling to 0° C., the gel was washed 8 times using approximately 50 ml of ice water. This resulted in 7.3 grams of gel. Of this, 3.3 grams were added to 15 ml of water, after which it was stirred at room temperature. After 10 minutes, 1 hour, 2 hours, 4 hours and overnight (a total of 1385 minutes), a sample was taken for analysis. Then, 100 µl of α-amylase were added (Termamyl, Novo Nordisk), after which it was stirred for 2 hours at room temperature. After 30, 60 and 120 minutes, a sample was taken for analysis. The part of the lysozyme present that was free in solution (in %) is shown in FIG. 4 as a function of time. It was found that, 10 minutes after adding the dry gel to the lysozyme solution, only 0.01% of the enzyme was free in solution. Also, 5 minutes after the wet and washed gel was added to water, only 0.01% of the lysozyme was not bound to the gel. After stirring for 4 hours at room temperature, this became 0.1%, and after stirring for a whole night at room temperature, this became 0.5%. Only half an hour after adding the α-amylase, the lysozyme activity was found to increase 40 times. That is 16% of what was present in the gel.

Example 52

Incorporating Lysozyme for Testing Purposes

To a solution of 170 mg of lysozyme in 15 ml of water, 203 mg of gel C were added. After stirring for 5 minutes at room temperature, the gel was washed 6 times using approximately 50 ml of ice water. Each time, the gel was isolated by means of centrifuging (3500 G). This resulted in 5.1 grams of gel. This sample is used in example 53.

Example 53

Effectiveness Against Tester Strain

To test the effectiveness of the polymer matrix in which an antimicrobial compound is comprised, a suspension of this matrix was dripped on an agar plate in which the tester strain is enclosed. By incubating the plate at 25° C., the tester strain will grow, except on the spot where the envelopes are being decomposed by microbial activity of the tester strain itself (amylase secretion). A successful inhibition of the microbial activity becomes manifest in the form of a clear ring (halo) around the spot where the envelopes were dripped on the plate.

Material and Method

| Test strain | | | |
|---|---|---|---|
| Name | Culture collection no. | Medium | Temp. |
| *Bacillus licheniformis* | LMG 7558 | yeast-starch agar | 25° C. |

The strain was grown on starch yeast extract agar and standardized to $OD_{650\,nm}$ 0.5 using PPS. This is the graft suspension. Of this, a $10^{-1}$ through $10^{-4}$ dilution was made. Before casting the plates (Ø15 cm, 50 ml of agar per plate), to the yeast-starch agar medium (nutrient agar +0.05% yeast extract +2% starch), per 100 ml, 1 ml of culture was added in the dilution of $10^{-2}$ per 100 ml (concentration in the agar 104 kve/ml). Per plate, 1 ml of test substance (100%, 90%, 80%, 70%, 60% and 50% respectively, suspension of starch globules with lysozyme in aqua dest.) was added and the plate was dried for 30 minutes. Then, the plates were incubated at 25° C. The halo formation was judged with the eye and photographed. All plates grafted using test substance showed a clear halo, from which it may be concluded that the antimicrobial substance has been released.

The invention claimed is:

1. Inducible release vehicle comprising a charged cross-linked polymer and an active component, wherein release of the active component does not occur in an aqueous medium until release is initiated by contact of the vehicle with a stimulus external to the vehicle, wherein said polymer is a carbohydrate consisting of only C-, O- and H-atoms, and wherein the stimulus external to the vehicle is an enzyme with specificity for the degradation of said polymer.

2. Vehicle according to claim 1 wherein the active ingredient is incorporated after the vehicle has been isolated.

3. Vehicle according to claim 2 wherein the carbohydrate polymer is modified by oxidation, substitution with carboxymethyl groups, or esterification.

4. Vehicle according to claim 1 wherein the release of the active ingredient is induced by change of electrostatic interaction.

5. Vehicle according to claim 1 wherein the polymer is chosen from the group consisting of starch, cellulose, and pectin.

6. Vehicle according to claim 1 wherein the cross linker is chosen from the group consisting of a divinyl sulphone, a epichlorohydrin, a di-epoxide, a sodium trimetaphosphate and an adipic acid.

7. Vehicle according to claim 1 wherein the polymer is cross-linked by means of a cross-linking enzyme chosen from the group consisting of peroxidases, laccases, polyphenol oxidases, and lipoxygenases.

8. Vehicle according to claim 1 wherein the vehicle is loaded with a charged compound.

9. Vehicle according to claim 1 wherein the vehicle is loaded with a hydrophobic compound.

10. Vehicle according to claim 8 wherein the vehicle is loaded with a protein or an anti microbial compound.

11. A pharmaceutical and/or nutraceutical composition comprising a vehicle according to claim 1.

12. A cosmetic composition comprising a vehicle according to claim 1, wherein the active component is an anti acne agent.

13. A cosmetic composition comprising a vehicle according to claim 1, wherein the active component is a deodorant.

14. A fungicidal paint comprising a vehicle according to claim 1, wherein the active component is a fungicide.

15. An antifouling paint composition comprising a vehicle according to claim 1, wherein the active component is an antifouling component.

16. A dressing means comprising a vehicle according to claim 1, wherein the dressing means is a wound dressing means or a sanitary dressing means and wherein the active component is an antimicrobial compound.

17. A medicine containing a vehicle according to claim 1, wherein the active component is an antimicrobial compound.

18. A medicine containing a vehicle according to claim 1, wherein the active component is a cytostatic agent.

19. A coating comprising a vehicle according to claim 1, wherein the active component is an antimicrobial compound.

20. A vehicle according to claim 1 which contains a flavoring agent.

21. A method for producing a vehicle according to claim 1 comprising:
    a) providing a polymer and a cross-linker or cross-linking enzyme;
    b) activating the cross-linking by addition of base or acid;
    c) allowing for cross-linking and gelation of the cross-linked polymer to occur;
    d) breaking the gel resulting from step c) into smaller particles;
    e) drying the particles from step d) and optionally grinding these into finer particles;
    f) loading said particles with an active component.

22. Vehicle according to claim 9 wherein the vehicle is loaded with a protein or an anti microbial compound.

23. Vehicle according to claim 8, wherein the charged compound has a molecular weight below 50 kD.

24. Vehicle according to claim 3, wherein the carbohydrate polymer is modified by esterification by acetyl groups.

25. Vehicle according to claim 4, wherein the change of electrostatic interaction is induced by a change in pH.

26. Vehicle according to claim 4, wherein the change of electrostatic interaction is induced by a change in the salt concentration.

27. Vehicle according to claim 20, wherein the flavoring agent is for a chewing gum.

28. Vehicle according to claim 1, wherein said enzyme is selected from the group consisting of amylase, hemicellulase, xylanase, glucanase, pullulanase, arabinodase, cellulase, pectinase, and mannanase, and wherein said polymer comprises glucose, fructose, sucrose, maltose, arabinose, mannose, galactose, lactose, cellulose, dextrin, agarose, amylose, amylopectin, or gum, or oligomers or polymers thereof.

29. Vehicle according to claim 6, wherein the di-epoxide is selected from the group consisting of glycerol diglycidyl ether and butanedioldiglycidyl ether.

30. Vehicle according to claim 1, wherein in a moist environment, the active component exists in an intact form within the vehicle until release of the active component from the vehicle is initiated by contact of the vehicle with the stimulus external to the vehicle.

* * * * *

UNITED STATES PATENT AND TRADEMARK OFFICE
CERTIFICATE OF CORRECTION

PATENT NO.         : 8,771,649 B2                                        Page 1 of 1
APPLICATION NO.    : 10/558816
DATED              : July 8, 2014
INVENTOR(S)        : Henricus Matheus Wilhelmus Maria Thijssen et al.

It is certified that error appears in the above-identified patent and that said Letters Patent is hereby corrected as shown below:

Title page of Patent, Item (75) Inventors, lines 6-7:

"Jacobus Johannes Frederick van Veen" should read

--Jacobus Johannes Frederik van Veen--

Signed and Sealed this
Eleventh Day of November, 2014

Michelle K. Lee
*Deputy Director of the United States Patent and Trademark Office*